United States Patent [19]

Fabry

[11] Patent Number: 5,789,372
[45] Date of Patent: Aug. 4, 1998

[54] SURFACTANT MIXTURES HAVING IMPROVED SURFACE-ACTIVE PROPERTIES

[75] Inventor: Bernd Fabry, Korschenbroich, Germany

[73] Assignee: Henkel Kommanditgesellschaft auf Aktien, Duesseldorf, Germany

[21] Appl. No.: 929,745

[22] PCT Filed: Jan. 3, 1995

[86] PCT No.: PCT/EP95/00008

§ 371 Date: Jun. 12, 1996

§ 102(e) Date: Jun. 12, 1996

[87] PCT Pub. No.: WO95/19415

PCT Pub. Date: Jul. 20, 1995

Related U.S. Application Data

[63] Continuation of Ser. No. 669,500, Jul. 12, 1995, abandoned.

[30] Foreign Application Priority Data

Jan. 12, 1994 [DE] Germany ............... 44 00 632.2

[51] Int. Cl.$^6$ .................. C11D 3/32; C11D 1/94; C11D 1/83

[52] U.S. Cl. ................ 510/502; 510/501; 510/514; 510/221; 510/223; 510/423; 510/433; 510/434; 510/470; 510/477; 510/475; 510/506

[56] References Cited

U.S. PATENT DOCUMENTS

| | | | |
|---|---|---|---|
| 1,985,424 | 12/1934 | Piggott | 260/124 |
| 2,016,962 | 10/1935 | Flint et al. | 260/127 |
| 2,703,798 | 3/1955 | Schwartz . | |
| 3,424,680 | 1/1969 | van Loo et al. | 252/8.8 |
| 3,424,681 | 1/1969 | Stanford | 252/8.55 |
| 5,009,814 | 4/1991 | Kelkenberg et al. | 252/548 |
| 5,376,310 | 12/1994 | Cripe et al. | 252/548 |
| 5,545,354 | 8/1996 | Ofosu-Asante | 510/237 |

FOREIGN PATENT DOCUMENTS

| | | |
|---|---|---|
| 285 768 | 2/1988 | European Pat. Off. . |
| 580 491 | of 0000 | France . |
| 89/68312 | 5/1989 | Japan . |
| 92/06158 | 4/1992 | WIPO . |
| 92/06160 | 4/1992 | WIPO . |
| WO 92/06984 | 4/1992 | WIPO . |
| WO 92/6152 | 4/1992 | WIPO . |
| WO 92/6153 | 4/1992 | WIPO . |
| WO 92/6154 | 4/1992 | WIPO . |
| WO 92/6155 | 4/1992 | WIPO . |
| WO 92/6156 | 4/1992 | WIPO . |
| WO 92/6157 | 4/1992 | WIPO . |
| WO 92/6158 | 4/1992 | WIPO . |
| WO 92/6159 | 4/1992 | WIPO . |
| WO 92/6160 | 4/1992 | WIPO . |
| WO 92/6161 | 4/1992 | WIPO . |
| WO 92/6162 | 4/1992 | WIPO . |
| WO 92/6164 | 4/1992 | WIPO . |
| WO 92/6170 | 4/1992 | WIPO . |
| WO 92/6171 | 4/1992 | WIPO . |
| WO 92/6172 | 4/1992 | WIPO . |

OTHER PUBLICATIONS

Tens.Surf.Det. 25, 8 (1988).
Surfactants in Consumer Products, Springer Verlag, Berlin, 1987, pp. 54–124.
J.Falbe (ed.), Katalysatoren, Tenside und Mineröladditive, Thieme Verlag, Stuttgart, 1978, pp. 123–127.
Kosmetische Färbemittel of the Farbstoffkommission der Deutschen Forschungsgemeinschaft, published by Verlag Chemie, Weinheim, 1984.
DIN 53902.
DIN 53901 (Replaced with ISO 8022).
Fette, Seifen, Anstrichmitt, 74, 163 (1972).

*Primary Examiner*—Paul Lieberman
*Assistant Examiner*—Charles Boyer
*Attorney, Agent, or Firm*—Ernest G. Szoke; Wayne C. Jaeschke; Real J. Grandmaison

[57] ABSTRACT

Surfactant mixtures having improved surface-active properties containing a) fatty acid-N-alkyl polyhydroxyalkylamides corresponding to formula (I):

$$R^1CO-\underset{\underset{R^2}{|}}{N}-[Z] \quad (I)$$

in which $R^1CO$ is an aliphatic acyl radical containing 6 to 10 carbon atoms, $R^2$ is hydrogen, an alkyl or hydroxyalkyl radical containing 1 to 4 carbon atoms and [Z] is a linear or branched polyhydroxyalkyl radical containing 3 to 12 carbon atoms and 3 to 10 hydroxyl groups, and b) fatty acid-N-alkyl polyhydroxyalkylamides corresponding to formula (II):

$$R^3CO-\underset{\underset{R^4}{|}}{N}-[Z] \quad (II)$$

in which $R^3CO$ is an aliphatic acyl radical containing 12 to 22 carbon atoms, $R^4$ is hydrogen, an alkyl or hydroxyalkyl radical containing 1 to 4 carbon atoms and [Z] is a linear or branched polyhydroxyalkyl radical containing 3 to 12 carbon atoms and 3 to 10 hydroxyl groups, the ratio by weight between components a) and b) being from 80:20 to 20:80.

21 Claims, No Drawings

SURFACTANT MIXTURES HAVING IMPROVED SURFACE-ACTIVE PROPERTIES

This application is a continuation, of application Ser. No. 08/669,500 filed on Jul. 12, 1995, now abandoned.

BACKGROUND OF THE INVENTION

1. Field of the Invention

This invention relates to surfactant mixtures with improved surface-active properties containing short-chain and long-chain fatty acid-N-alkyl polyhydroxyalkylamides in selected synergistic mixing ratios.

2. Discussion of Related Art

Fatty acid-N-alkyl polyhydroxyalkylamides are nonionic surfactants which may normally be obtained by reductive amination of a reducing sugar with ammonia, an alkylamine or an alkanolamine and subsequent acylation with a fatty acid, a fatty acid alkyl ester or a fatty acid chloride. Particulars of processes for their production can be found in U.S. Pat. No. 1,985,424, U.S. Pat. No. 2,016,962 and U.S. Pat. No. 2,703,798 and in International patent application WO 92/06984. A review of this subject by H. Kelkenberg can be found in Tens. Surf. Det. 25, 8 (1988).

The fatty acid-N-alkyl polyhydroxyalkylamides are preferably derived from reducing sugars containing 5 or 6 carbon atoms, more particularly from glucose. Accordingly, the preferred fatty acid-N-alkyl polyhydroxyalkylamides are fatty acid-N-alkyl glucamides.

Fatty acid-N-alkyl glucamides have been used for some time in manual dishwashing detergents as mild nonionic surfactants with favorable foaming and cleaning power. The use of these substances is the subject of a number of publications. For example, their use as thickeners is known from European patent application EP-A1 0 285 768 (Huls). FR-A 1 580 491 (Henkel) describes water-containing detergent mixtures based on sulfates and/or sulfonates, nonionic surfactants and optionally soaps which contain fatty acid-N-alkyl glucamides as foam regulators.

International patent applications WO 9216153; 6156; 6157; 6158; 6159 and 6160 (Procter & Gamble) describe mixtures of fatty acid-N-alkyl glucamides with anionic surfactants, surfactants of sulfate and/or sulfonate structure, ether carboxylic acids, ether sulfates, methyl ester sulfonates and nonionic surfactants. The use of these substances in various laundry detergents, dishwashing detergents and cleaning compositions is described in International patent applications WO 92/6152; 6154; 6155; 6161; 6162; 6164; 6170; 6171 and 6172 (Procter & Gamble).

Despite this comprehensive prior art, there is still a need for fatty acid-N-alkyl polyhydroxyalkylamides with improved properties, more especially greater foaming power, even in hard water, better wetting times, increased washing power and greater dermatological compatibility.

Accordingly, the problem addressed by the present invention was to provide fatty acid-N-alkyl polyhydroxyalkylamides which would satisfy the required complex property profile.

DESCRIPTION OF THE INVENTION

The present invention relates to surfactant mixtures with improved surface-active properties containing a) fatty acid-N-alkyl polyhydroxyalkylamides corresponding to formula (I):

in which $R^1CO$ is an aliphatic acyl radical containing 6 to 10 carbon atoms, $R^2$ is hydrogen, an alkyl or hydroxyalkyl radical containing 1 to 4 carbon atoms and [Z] is a linear or branched polyhydroxyalkyl radical containing 3 to 12 carbon atoms and 3 to 10 hydroxyl groups, and b) fatty acid-N-alkyl polyhydroxyalkylamides corresponding to formula

in which $R^3CO$ is an aliphatic acyl radical containing 12 to 22 carbon atoms, $R^4$ is hydrogen, an alkyl or hydroxyalkyl radical containing 1 to 4 carbon atoms and [Z] is a linear or branched polyhydroxyalkyl radical containing 3 to 12 carbon atoms and 3 to 10 hydroxyl groups, the ratio by weight between component a) and b) being from 80:20 to 20:80.

It has surprisingly been found that short-chain and relatively long-chain fatty acid-N-alkyl polyhydroxyalkylamides, more especially fatty acid-N-alkyl glucamides, synergistically complement one another in regard to their foaming, wetting and washing power and their dermatological compatibility within certain mixing ranges.

Fatty Acid-N-Alkyl Polyhydroxyalkylamides

As already mentioned, the fatty acid-N-alkyl polyhydroxyalkylamides are known nonionic surfactants which may be obtained by relevant known processes as mentioned above.

The fatty acid-N-alkyl polyhydroxyalkylamides are preferably derived from reducing sugars containing 5 or 6 carbon atoms, more especially from glucose. Accordingly, the preferred fatty acid-N-alkyl polyhydroxyalkylamides are fatty acid-N-alkyl glucamides corresponding to formula (III):

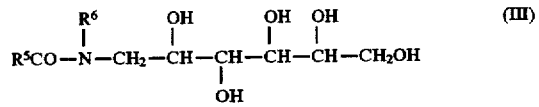

in which $R^5CO$ and $R^6$ are as defined for formulae (I) and (II). In addition, the polyhydroxyalkylamides may also be derived from maltose and palatinose.

The substances of component a) preferably correspond to fatty acid-N-alkyl glucamides of formula (I) in which $R^1CO$ is a saturated acyl radical containing 8 to 10 carbon atoms and $R^2$ is a methyl radical. Typical examples are fatty acid-N-methyl glucamides derived from caprylic acid, 2-ethyl hexanoic acid and/or capric acid and technical mixtures thereof. It is particularly preferred to use a methyl glucamide based on a technical $C_{8-10}$ fatty acid which is obtained, for example as first runnings in the distillation of cocofatty acid.

The substances of component b) preferably correspond to fatty acid-N-alkyl glucamides of formula (II) in which $R^3CO$ is a saturated acyl radical containing 12 to 18 carbon atoms and, more particularly, 12 to 14 carbon atoms and $R^4$ is a methyl radical. Typical examples are fatty acid-N-alkyl glucamides derived from lauric acid, myristic acid, palmitic acid, palmitoleic acid, stearic acid, isostearic acid, oleic acid, elaidic acid, petroselic acid, linoleic acid, linolenic acid and technical mixtures thereof. It is particularly preferred to use a methyl glucamine based on a technical $C_{12-14}$ cocofatty acid fraction.

The components a) and b) may be present in the surfactant mixtures in ratios by weight of 80:20 to 20:80 and preferably in ratios by weight of 75:25 to 25:75. A ratio of a) to b) of 20:80 to 50:50 is particularly preferred, a ratio of 25:75 to 40:60 being most particularly preferred. In other words, the greatest synergisms are achieved when relatively short-chain homologs are added to the relatively long-chain fatty acid-N-alkyl glucamides in quantities of 20 to 50% by weight and preferably in quantities of 25 to 40% by weight.

Other Surfactants

The surfactant mixtures according to the invention may contain other anionic, nonionic, cationic and/or amphoteric or zwitterionic surfactants, the percentage content of components a) and b) in these at least ternary mixtures preferably amounting to between 25 and 75% by weight and more preferably to between 40 and 60% by weight, based on the mixtures.

Typical examples of anionic surfactants are alkyl benzene sulfonates, alkane sulfonates, olefin sulfonates, alkyl ether sulfonates, glycerol ether sulfonates, α-methyl ester sulfonates, sulfofatty acids, alkyl sulfates, fatty alcohol ether sulfates, glycerol ether sulfates, hydroxy mixed ether sulfates, monoglyceride sulfates, fatty acid amide (ether) sulfates, sulfosuccinates, sulfotriglycerides, amide soaps, ether carboxylic acids, fatty acid isethionates, sarcosinates, taurides, alkyl oligoglucoside sulfates, alkyl (ether) phosphates, acyl lactylates and vegetable or animal protein hydrolyzates or condensation products thereof with fatty acids. If the anionic surfactants contain polyglycol ether chains, they may have a conventional homolog distribution, although they preferably have a narrow homolog distribution.

Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, alk(en)yl oligoglycosides, polyol fatty acid esters, sugar esters, sorbitan esters and polysorbates. If the nonionic surfactants contain polyglycol ether chains, they may have a conventional homolog distribution although they preferably have a narrow homolog distribution.

Typical examples of cationic surfactants are quaternary ammonium compounds and quaternized fatty acid trialkanolamine esters.

Typical examples of amphoteric or zwitterionic surfactants are alkyl betaines, alkyl amidobetaines, aminopropionates, aminoglycinates, imidazolinium betaines and sulfobetaines.

The surfactants mentioned are all known compounds. Particulars of their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside und mineralöladditive", Thieme Verlag, Stuttgart, 1978, pages 123 to 217.

The water-containing detergent mixtures may be prepared simply by mechanically mixing the aqueous solutions of the components, optionally at elevated temperatures of 30° to 50° C.; no chemical reaction is involved.

Surface-Active Formulations

Further subjects to which the invention also relates are described in the following:

Powder-form universal detergents containing 10 to 30% by weight, based on the detergent, of the surfactant mixtures according to the invention and optionally other auxiliaries and additives.

Liquid universal detergents containing 10 to 70% by weight, based on the detergent, of the surfactant mixtures according to the invention and optionally other auxiliaries and additives.

Liquid liglht-duty detergents containing 10 to 50% by weight, based on the detergent, of the surfactant mixtures according to the invention and optionally other auxiliaries and additives.

Liquid cleaners and disinfectants containing 10 to 30% by weight, based on the detergent, of the surfactant mixtures according to the invention and optionally other auxiliaries and additives.

Manual dishwashing detergents containing 5 to 25% by weight, based on the detergent, of the surfactant mixtures according to the invention and optionally other auxiliaries and additives. Particularly preferred manual dishwashing detergents contain 5 to 10% by weight of the surfactant mixtures according to the invention, 5 to 10% by weight of fatty alcohol ether sulfates, 1 to 5% by weight of alkyl betaines and/or 1 to 5% by weight of alkyl oligoglucosides.

Machine dishwashing detergents containing 5 to 25% by weight, based on the detergent, of the surfactant mixtures according to the invention and optionally other auxiliaries and additives.

Rinse aids containing 10 to 50% by weight, based on the rinse aid, of the surfactant mixtures according to the invention and optionally other auxiliaries and additives.

Fabric softeners containing 2 to 35% by weight, based on the fabric softener, of the surfactant mixtures according to the invention and optionally other auxiliaries and additives.

Hair shampoos containing 10 to 30% by weight, based on the shampoo, of the surfactant mixtures according to the invention and optionally other auxiliaries and additives.

Hair rinses containing 10 to 30% by weight, based on the hair rinse, of the surfactant mixtures according to the invention and optionally other auxiliaries and additives.

Foam baths containing 10 to 30% by weight, based on the foam bath, of the surfactant mixtures according to the invention and optionally other auxiliaries and additives.

Syndet soaps containing 10 to 50% by weight, based on the syndet soap, of the surfactant mixtures according to the invention and optionally other auxiliaries and additives.

Collectors for the flotation of non-sulfidic ores containing 10 to 95% by weight, based on the collector, of the surfactant mixtures according to the invention and optionally other auxiliaries and additives.

Detergents based on the detergent mixtures according to the invention may contain, for example, builders, salts, bleaching agents, bleach activators, optical brighteners, redeposition inhibitors, soil repellants, solubilizers, foam inhibitors and enzymes as auxiliaries and additives.

Typical builders are sodium aluminium silicates (zeolites), phosphates, phosphonates, ethylenediamine tetraacetic acid, nitrilotriacetate, citric acid and/or polycarboxylates. Suitable salts or fillers are, for example, sodium sulfate, sodium carbonate or sodium silicate (waterglass). Typical individual examples of other additives are sodium borate, starch, sucrose, polydextrose, TAED, stilbene compounds, methyl cellulose, toluene sulfonate, cumene sulfonate, long-chain soaps, silicones, mixed ethers, lipases and proteases.

Typical soil repellants are polymers preferably containing ethylene terephthalate and/or polyethylene glycol terephthalate groups, the molar ratio of ethylene terephthalate to polyethylene glycol terephthalate being in the range from 50:50 to 90:10. The molecular weight of the linking polyethylene glycol units is preferably in the range from 750 to 5,000, i.e. the degree of ethoxylation of the polymers containing polyethylene glycol groups may be from about 15 to 100. The polymers are distinguished by an average molecular weight of around 5,000 to 200,000 and may have a block structure, although they preferably have a random structure. Examples of commercially available polymers are the products Milease® T (ICI) or Repelotex® SRP 3 (Rhome-Poulenc).

Hair shampoos, hair lotions or foam baths based on the detergent mixtures according to the invention may contain, for example, emulsifiers, oil components, fats and waxes, thickeners, superfatting agents, biogenic agents, film formers, fragrances, dyes, pearlescing agents, preservatives and pH regulators as auxiliaries and additives.

Suitable oils are, for example, Guerbet alcohols based on fatty alcohols containing 6 to 18 and preferably 8 to 10 carbon atoms, esters of linear $C_{6-20}$ fatty acids with linear $C_{6-20}$ fatty alcohols, esters of branched $C_{6-13}$ carboxylic acids with linear $C_{16-18}$ fatty alcohols, esters of linear $c_{10-18}$ fatty acids with branched alcohols, more especially 2-ethyl hexanol, esters of linear and/or branched fatty acids with dihydric alcohols and/or Guerbet alcohols, triglycerides based on $C_{6-10}$ fatty acids, vegetable oils, branched primary alcohols, substituted cyclohexanes and/or dialkyl ethers.

Suitable emulsifiers are both known w/o and o/w emulsifiers. Typical examples of fats are glycerides while suitable waxes are inter alia beeswax, paraffin wax or microwaxes. Suitable thickeners are, for example, cross-linked polyacrylic acids and derivatives thereof, polysaccharides, more especially xanthan gum, guar guar, agar agar, alginates and tyloses, carboxymethyl cellulose and hydroxyethyl cellulose, fatty alcohols, mono-glycerides and fatty acids, polyacrylates, polyvinyl alcohol and polyvinyl pyrrolidone. Suitable biogenic agents are, for example, plant extracts, protein hydrolyzates and vitamin complexes. Typical film formers are, for example, polyvinyl pyrrolidone, vinyl pyrrolidone/vinyl acetate copolymers, polymers of the acrylic acid series, quaternary cellulose derivatives and similar compounds. Suitable preservatives are, for example, formaldehyde solution, p-hydroxybenzoate or sorbic acid. Suitable pearlescing agents are, for example, glycol distearic acid esters, such as ethylene glycol distearate, and also fatty acids and fatty acid monoglycol esters. The dyes used may be any of the substances suitable and permitted for cosmetic purposes, as listed for example in the publication "Kosmetische Färbemittel" of the Farbstoffkommission der Deutschen Forschungsgemeinschaft, published by Verlag Chemie, Weinheim, 1984. These dyes are normally used in concentrations of 0.001 to 0.15 by weight, based on the mixture as a whole.

The total quantity of auxiliaries and additives may be from 1 to 50% by weight and is preferably from 5 to 40% by weight, based on the formulation.

The formulations may be produced in known manner, i.e. for example by hot, cold, hot-hot/cold or PIT emulsification. These are purely mechanical processes which do not involve any chemical reaction.

Commercial Applications

The surfactant mixtures according to the invention are distinguished by synergistic enhancement of the washing, dishwashing, foaming and cleaning performance and by advantageous skin-cosmetic and ecotoxicological compatibility. A minimum of the total irritation scores and hence an optimum of dermatological compatibility were observed for mixing ratios between components a) and b) of 20:80 to 50:50 and preferably 25:75 to 40:60.

Accordingly, the present invention also relates to the use of the surfactant mixtures according to the invention for the production of laundry detergents, dishwashing detergents, cleaning compositions, fabric softeners and flotation auxiliaries, hair-care and body-care products, in which they may be present in quantities of 1 to 99% by weight and preferably in quantities of 10 to 30% by weight, based on the particular formulation.

EXAMPLES

1. Surfactants Used

A1) $C_{8-10}$ head-fractionated fatty acid-N-methyl glucamide
A2) $C_{12-14}$ cocofatty acid-N-methyl glucamide
A3) Mixture of A1) and A2) in a ratio by weight of 25:75
A4) Mixture of A1) and A2) in a ratio by weight of 40:60
B1) Dodecyl benzene sulfonate Na salt (Maranil® A 55)
B2) $C_{16/18}$ tallow fatty acid sulfate Na salt (Sulfopon® T 50)
B3) $C_{12/14}$ cocofatty alcohol 3.6 EO sulfate Na salt (Texapon® K14S)
B4) Alpha-sulfo $C_{16/18}$ tallow fatty acid methyl ester Na salt (Texine® ES 68)
B5) $C_{12/14}$ cocofatty alcohol 2.5 EO adduct, narrow-range (Arlypon® F-NRE)
B6) $C_{12/14}$ cocoalkyl oligoglucoside (Plantaren® APG 600 UP).

II. Performance Tests

A) Evaluation of Foaming Power (FP).

Foaming power was evaluated by the Götte foam generation method according to DIN 53902, Part 1. 1% by weight surfactant solutions in water with a hardness of 160° were used; the temperature was 20° C. The results of the foam tests, expressed as the basic foam volume in ml, are set out in Table 1.

B) Evaluation of Wetting Power (WP).

Wetting power was evaluated by the immersion wetting method according to DIN 53901. 1% by weight surfactant solutions in water with a hardness of 16° were used; the temperature was 20° C. The results of the wetting tests, expressed as the wetting time in s, are set out in Table 1.

C) Evaluation of Dishwashing Performance (DWP).

Dishwashing performance was evaluated by the saucer test [Fette, Seifen, Anstrichmitt., 74, 163 (1972)]. To this end, saucers 14 cm in diameter were each soiled with 2 ml of beef tallow (acid value 9–10) and stored for 24 h at room temperature. The saucers were then washed with 5 liters of tap water (hardness 16° d.) at 50° C. The test mixture was used in a quantity of 0.15 g of active substance/l. The dishwashing test was terminated when the foam had completely disappeared from the surface. The results of the dishwashing tests, expressed as the number of clean saucers, are set out in Table 1.

D) Evaluation of Washing Performance (WP).

Washing performance was tested in a Launderometer against a dust/sebum soil on polyester/cotton (crease-resistant) fabric at 40° C. The lightening of the washed fabric was evaluated by photometric reflectance measurement using an Elrepho RFC 3/24 against a barium sulfate standard of which the reflectance was put at 100%. The results are expressed as percentage reflectance (%-R).

Liquor : 250 ml
Liquor load : 1 part by weight fabric/30 parts by weight water

Dosage : 10 g/l
Water hardness : 16° d.
Determination : average of 3 measurements
The results of the washing tests are set out in Table 1.

TABLE 1

| | | | | Performance Tests | | | |
|---|---|---|---|---|---|---|---|
| Ex. | Surfactants | | Ratio | FP ml | WP s | DWP | WP %-R |
| 1 | A1 | A2 | 0:100 | 350 | 150 | 8 | 55 |
| | A1 | A2 | 10:90 | 400 | 145 | 10 | 59 |
| | A1 | A2 | 25:75 | 575 | 95 | 15 | 60 |
| | A1 | A2 | 40:60 | 600 | 93 | 16 | 63 |
| | A1 | A2 | 50:50 | 550 | 102 | 14 | 63 |
| | A1 | A2 | 60:40 | 525 | 109 | 14 | 63 |
| | A1 | A2 | 80:20 | 510 | 111 | 14 | 63 |
| | A1 | A2 | 90:10 | 500 | 115 | 12 | 59 |
| | A1 | A2 | 100:0 | 500 | 120 | 12 | 57 |
| 2 | A3 | B1 | 50:50 | 600 | 35 | 18 | 64 |
| | A3 | B2 | 50:50 | 580 | 90 | 16 | 65 |
| | A3 | B3 | 50:50 | 650 | 75 | 20 | 60 |
| | A3 | B4 | 50:50 | 580 | 89 | 16 | 65 |
| | A3 | B5 | 50:50 | 450 | 90 | 14 | 66 |
| | A3 | B6 | 50:50 | 635 | 90 | 19 | 60 |
| 3 | A4 | B1 | 40:60 | 625 | 25 | 18 | 65 |
| | A4 | B2 | 40:60 | 580 | 90 | 16 | 65 |
| | A4 | B3 | 40:60 | 675 | 75 | 21 | 60 |
| | A4 | B4 | 40:60 | 580 | 85 | 16 | 65 |
| | A4 | B5 | 40:60 | 490 | 90 | 14 | 65 |
| | A4 | B6 | 40:60 | 625 | 90 | 20 | 60 |

Legend: Ratio = Ratio by weight of the surfactants used

What is claimed is:

1. Surfactant mixtures having improved surface-active properties consisting essentially of a) fatty acid-N-polyhydromyalkylamides corresponding to formula (I):

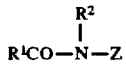

$$R^1CO-N-Z \quad \text{with } R^2 \text{ (I)}$$

in which $R^1CO$ is an aliphatic acyl radical containing 6 to 10 carbon atoms. $R^2$ is hydrogen, an alkyl or hydroxyalkyl radical containing 1 to 4 carbon atoms and Z is a linear or branched polyhydroxyalkyl radical containing 3 to 12 carbon atoms and 3 to 10 hydroxyl groups, and b) fatty acid-N-polyhydroxyalkylamides corresponding to formula (II):

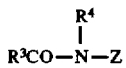

$$R^3CO-N-Z \quad \text{with } R^4 \text{ (II)}$$

in which $R^3CO$ is an aliphatic acyl radical containing 12 to 22 carbon atoms, $R^4$ is hydrogen, an alkyl or hydroxyalkyl radical containing 1 to 4 carbon atoms and Z is a linear or branched polyhydroxyalkyl radical containing 3 to 12 carbon atoms and 3 to 10 hydroxyl groups, the ratio by weight between components a) and b) being from 75:25 to 25:75.

2. Surfactant mixtures as in claim 1 wherein said component a) consists essentially of a fatty acid-N-alkyl glucamide corresponding to formula (I), in which $R^1CO$ is a saturated acyl radical containing 8 to 10 carbon atoms and $R^2$ is a methyl radical.

3. Surfactant mixtures as in claim 1 wherein said component b) consists essentially of a fatty acid-N-alkyl glucamide corresponding to formula (II), in which $R^2CO$ is a saturated acyl radical containing 12 to 16 carbon atoms and $R^4$ is a methyl radical.

4. Surfactant mixtures as in claim 2 wherein said component b) consists essentially of a fatty acid-N-alkyl glucamide corresponding to formula (II), in which $R^3CO$ is a saturated acyl radical containing 12 to 16 carbon atoms and $R^4$ is a methyl radical.

5. Surfactant mixtures as in claim 1 containing 25% to 75% by weight of said components a) and b), and the balance, anionic, nonionic, cationic, amphoteric or zwitterionic surfactants.

6. Surfactant mixtures as in claim 5 wherein said anionic surfactants are selected from the group consisting of alkyl benzene sulfonates, alkane sulfonates, olefin sulfonates, alkyl ether sulfonates, glycerol ether sulfonates, α-methyl ester sulfonates, sulfofatty acids, alkyl sulfates, fatty alcohol ether sulfates, glycerol ether sulfates, hydroxy mixed ether sulfates, monoglyceride (ether) sulfates, fatty acid amide (ether) sulfates, sulfosuccinates, sulfotriglycerides, amide soaps, ether carboxylic acids, fatty acid isethionates, sarcosinates, taurides, alkyl oligoglucoside sulfates, alkyl (ether) phosphates, acyl lactylates and vegetable or animal protein hydrolyzates or condensation products thereof with fatty acids.

7. Surfactant mixtures as in claim 5 wherein said nonionic surfactants are selected from the group consisting of fatty alcohol polyglycol ethers, alkylphenol polyglycol ethers, fatty acid polyglycol esters, fatty acid amide polyglycol ethers, fatty amine polyglycol ethers, alkoxylated triglycerides, alk(en)yl oligoglycosides, polyol fatty acid esters, sugar esters, sorbitan esters and polysorbates.

8. Surfactant mixtures as in claim 5 wherein said cationic surfactants are selected from the group consisting of quaternary ammonium compounds and quaternized fatty acid trialkanolamine esters.

9. Surfactant mixtures as in claim 5 wherein said amphoteric or zwitterionic surfactants are selected from the group consisting of alkyl betaines, alkyl amidobetaines, aminopropionates, aminoglycinates, imidazolinium betaines and sulfobetaines.

10. A granular detergent composition containing 10% to 30% by weight, based on the weight of said detergent composition, of the surfactant mixtures of claim 1.

11. A liquid detergent composition containing 10% to 70% by weight, based on the weight of said detergent composition, of the surfactant mixtures of claim 1.

12. A liquid light-duty detergent composition containing 10% to 50% by weight, based on the weight of said detergent composition of the surfactant mixtures of claim 1.

13. Liquid cleaner and disinfectant compositions containing 10% to 30% by weight, based on the weight of said compositions, of the surfactant mixtures of claim 1.

14. Manual dishwashing detergent compositions containing 5% to 25% by weight, based on the weight of said detergent compositions, of the surfactant mixtures of claim 1.

15. Machine dishwashing detergent compositions containing 5% to 25% by weight, based on the weight of said detergent compositions, of the surfactant mixtures of claim 1.

16. Rinse aid compositions containing 10% to 50% by weight, based on the weight of said rinse aid compositions, of the surfactant mixtures of claim 1.

17. Fabric softener compositions containing 2% to 35% by weight, based on the weight of said fabric softener compositions, of the surfactant mixtures of claim 1.

18. Hair shampoo compositions containing 10% to 30% by weight, based on the weight of said shampoo compositions, of the surfactant mixtures of claim 1.

19. Hair rinse compositions containing 10% to 30% by weight, based on the weight of said hair rinse compositions, of the surfactant mixtures of claim 1.

20. Bubble bath compositions containing 10% to 30% by weight, based on the weight of said bubble bath compositions, of the surfactant mixtures of claim 1.

21. Syndet soap compositions containing 10% to 50% by weight, based on the weight of said syndet soap compositions, of the surfactant mixtures of claim 1.

* * * * *